United States Patent
Koch

(10) Patent No.: US 6,795,725 B2
(45) Date of Patent: Sep. 21, 2004

(54) METHOD AND APPARATUS FOR ENDOSCOPIC MEASUREMENT OF MYOELECTRICAL ACTIVITY FROM THE STOMACH AND OTHER HOLLOW INTRA-ABDOMINAL ORGANS

(75) Inventor: Kenneth L. Koch, Hershey, PA (US)

(73) Assignee: 3PCM Company, Crystal Bay, NV (US)

( * ) Notice: Subject to any disclaimer, the term of this patent is extended or adjusted under 35 U.S.C. 154(b) by 0 days.

(21) Appl. No.: 10/315,017

(22) Filed: Dec. 10, 2002

(65) Prior Publication Data

US 2003/0114770 A1 Jun. 19, 2003

Related U.S. Application Data

(60) Provisional application No. 60/340,479, filed on Dec. 18, 2001.

(51) Int. Cl.[7] .................................................. A61B 5/04
(52) U.S. Cl. ........................ 600/546; 600/529; 600/593
(58) Field of Search ................................ 600/101, 104, 600/372, 374, 393, 433, 435, 529, 546, 587, 593; 606/41, 46; 607/6, 20

(56) References Cited

U.S. PATENT DOCUMENTS

| | | | |
|---|---|---|---|
| 5,109,870 A | 5/1992 | Silny et al. | |
| RE35,880 E | * 8/1998 | Waldman et al. | ............ 600/374 |
| 5,861,014 A | 1/1999 | Familoni | |
| 6,006,755 A | 12/1999 | Edwards | |
| 6,351,665 B1 | 2/2002 | Koch | |
| 6,613,047 B2 | * 9/2003 | Edwards | ........................ 606/41 |
| 2002/0071474 A1 | * 6/2002 | Werneth | ...................... 374/179 |
| 2002/0111560 A1 | 8/2002 | Kokate et al. | |

* cited by examiner

Primary Examiner—Charles Marmor
(74) Attorney, Agent, or Firm—Manelli Denison & Selter; Edward J. Stemberger

(57) ABSTRACT

A catheter structure includes an elongated tube structure having distal and proximal ends and an axis. Electrodes are associated with the tube structure and are constructed and arranged to be moved from a retracted position substantially within the tube structure to an extended position extended directly outwardly from the distal end of the tube structure and generally in the direction of the axis. The electrodes are constructed and arranged to obtain signals relating to myoelectrical activity of an intra-abdominal organ. Actuating structure is operatively associated with the electrodes to move the electrodes between the extended and retracted positions.

19 Claims, 2 Drawing Sheets

METHOD AND APPARATUS FOR ENDOSCOPIC MEASUREMENT OF MYOELECTRICAL ACTIVITY FROM THE STOMACH AND OTHER HOLLOW INTRA-ABDOMINAL ORGANS

This Application is based on U.S. Provisional Application No. 60/340,479, filed Dec. 18, 2001, and claims the benefit thereof for priority purposes.

FIELD OF THE INVENTION

The invention relates to a device for recording myoelectric activity of a human organ and, more particularly, to a catheter structure having electrodes that are delivered into the human organ to record myoelectric activity of the organ.

BACKGROUND OF THE INVENTION

Gastric myoelectrical activity comprises slow waves or pacesetter potentials and, action potential activity. The recording or measurement of gastric pacesetter potentials is presently accomplished with either electrodes sewn to the stomach serosa, an invasive procedure that requires surgery, or with electrodes placed on the abdominal surface. The electrodes placed on the abdominal surface record electrogastrograms or EGGs. These non-invasive recordings indicate the presence of normal 3-cpm activity at baseline and in response to a variety of foods or drugs.

Patients with unexplained dyspepsia symptoms or unexplained nausea and vomiting often have no obvious cause for these symptoms. No peptic ulcer disease, reflux disease or gallbladder abnormalities are found. Gastric dysrhythmias are frequent pathophysiological findings in these patients. Gastric dysrhythmias are termed bradygastrias (1.0–2.5 cpm) and tachygastrias (3.7–10.0 cpm). These gastric dysrhythmias have been defined in many different patient groups where dyspepsia symptoms are present. They have been recorded by serosal, mucosal and cutaneous electrode recordings.

The disadvantage of the EGG is that the signal must pass through the abdominal wall and adipose tissue before it is recorded. The EGG signal is also subject to movement artifact (errors). The disadvantage of the placement of electrodes on the serosa of the stomach is that surgical procedures are required that vary from a laparotomy to laparoscopic surgery. Furthermore, electrode wires must be brought to the surface through wounds in the abdominal wall. The disadvantage of the mucosal electrodes is that they are clipped onto the mucosa and frequently become dislodged during gastric contractions.

Accordingly, there is a need to provide a catheter structure that can be placed into the human organ under direct vision via an endoscope to record myoelectric activity of the organ.

SUMMARY OF THE INVENTION

An object of the invention is to fulfill the need referred to above. In accordance with the principles of the present invention, this objective is achieved by providing a catheter structure including an elongated tube structure having distal and proximal ends and an axis. Electrodes are associated with the tube structure and are constructed and arranged to be moved from a retracted position substantially within the tube structure to an extended position extended directly outwardly from the distal end of the tube structure and generally in the direction of the axis. The electrodes are constructed and arranged to obtain signals relating to myoelectrical activity of an intra-abdominal organ. Actuating structure is operatively associated with the electrodes to move the electrodes between the extended and retracted positions.

In accordance with another aspect of the invention, a method is provided for obtaining myoelectric activity from an intra-abdominal body organ having an internal cavity and a lining. The method provides catheter structure including an elongated tube structure having distal and proximal ends and an axis. Electrodes are associated with the tube structure and are constructed and arranged to be moved from a retracted position substantially within the tube structure to an extended position extended directly outwardly from the distal end of the tube structure and generally in the direction of the axis. The electrodes are constructed and arranged to obtain signals relating to myoelectrical activity of an intra-abdominal organ of a patient. Actuating structure is operatively associated with the electrodes to move the electrodes between the extended and retracted positions. The tube structure is inserted into the internal cavity of the organ, with the electrodes being in a retracted position with respect to the distal end of the tube structure. The actuating structure is moved to move the electrodes to the extended position to impinge on the lining of the organ. A respiration sensor is provided to monitor respiration of the patient. Signals from the electrodes indicative of myoelectrical activity of the organ are recorded. In addition, signals from the respiration sensor are recorded to determine when artifact occurs.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings, wherein like reference numerals refer to like parts, in which.

DETAILED DESCRIPTION OF THE EXEMPLARY EMBODIMENTS

Figure 1:
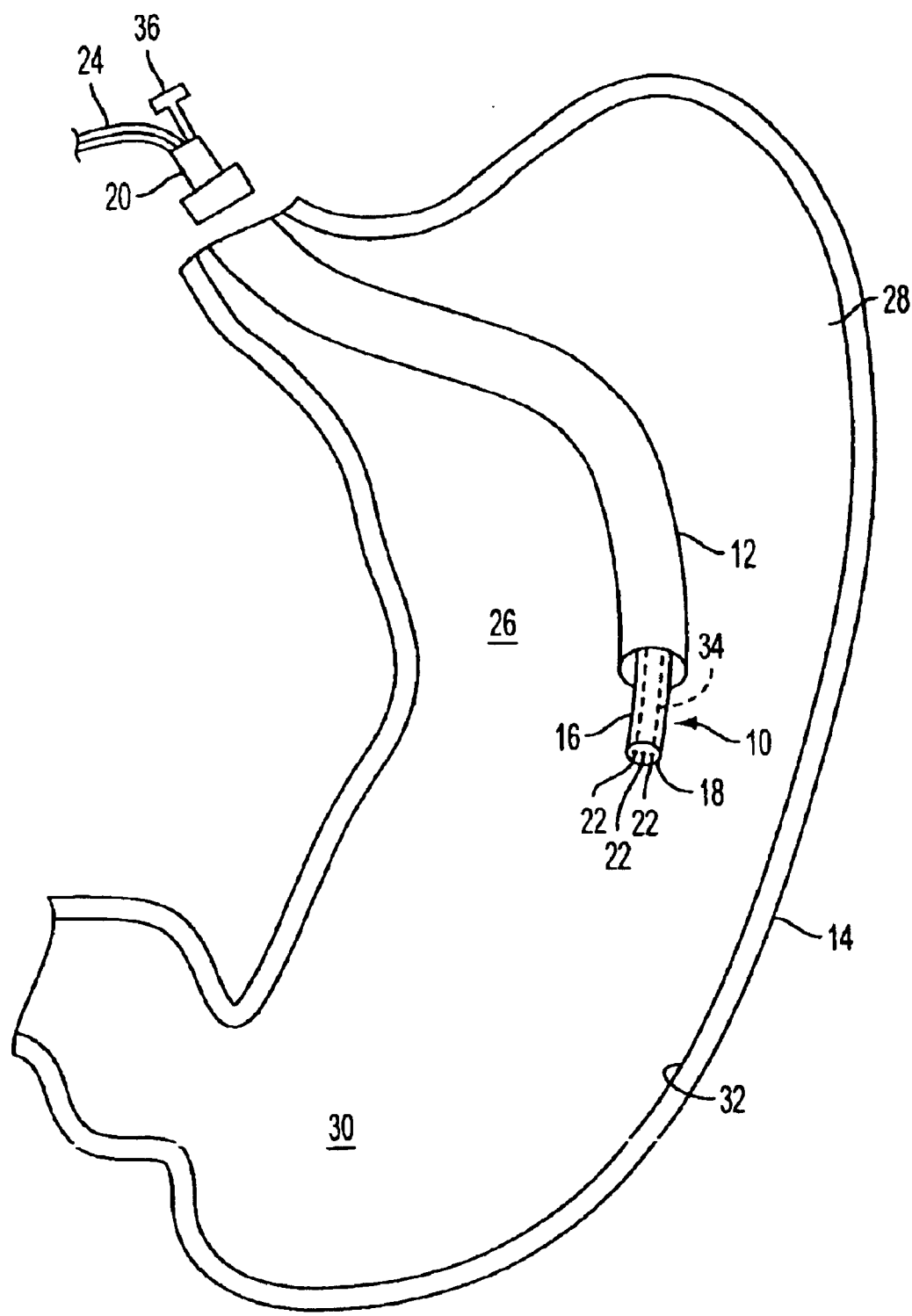
FIG. 1 is perspective view of a catheter structure, provided in accordance with the principles of the invention, shown being inserted into a stomach with electrodes thereof in a retracted, insertion position.
Figure 2:
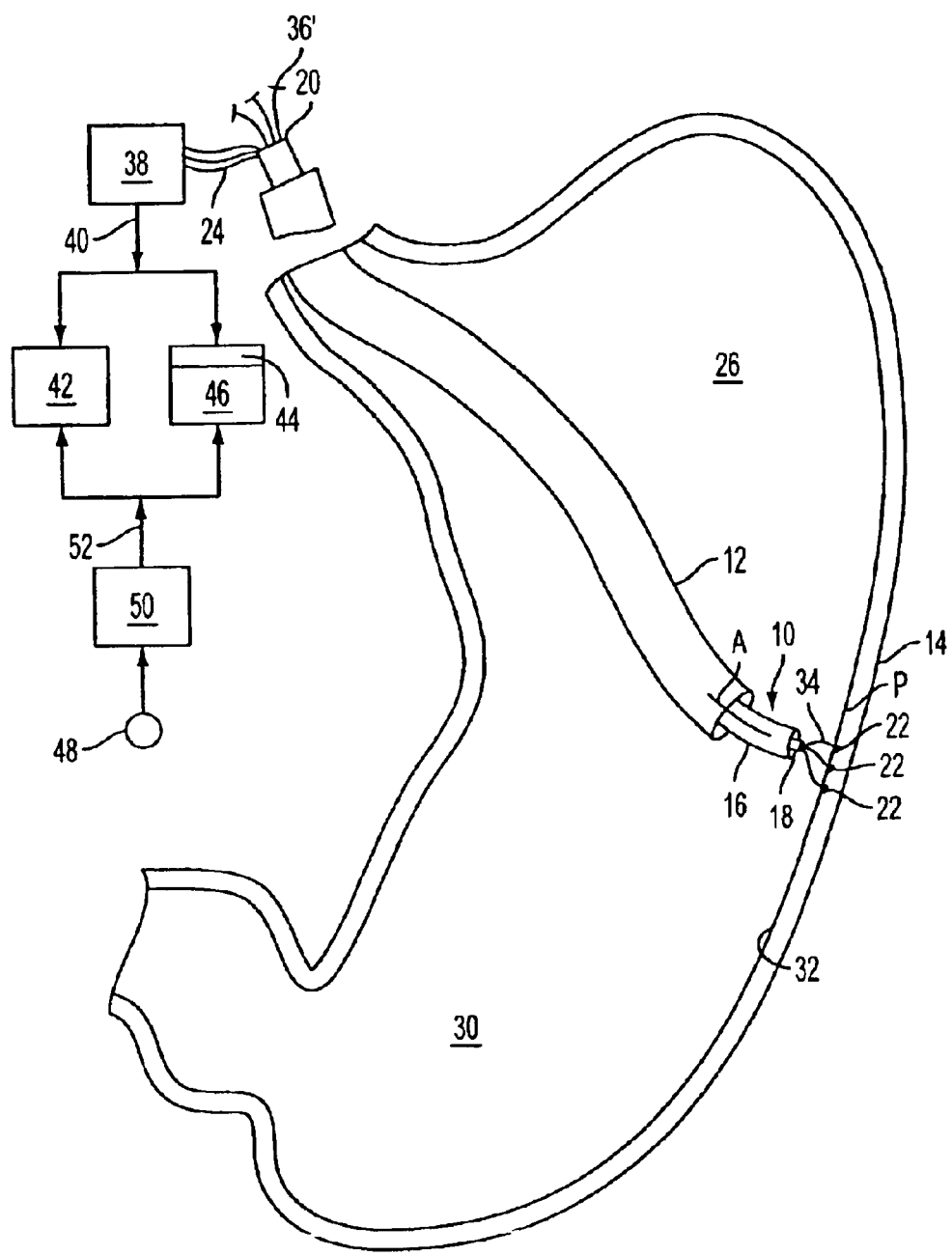
FIG. 2 is perspective view of the catheter structure of FIG. 1, shown within the stomach with the electrodes in an operative, extended position.

With reference to FIGS. 1 and 2, a catheter structure, provided in accordance with the invention, is shown generally indicated at 10 inserted via an endoscope 12 into a human organ, such as a stomach 14. The catheter structure 10 includes an elongated tube structure 16 having a distal end 18 and a proximal end 20. At least two electrodes 22 (three are shown in the embodiment) are associated with the tube structure 16 so as to be moved from a substantially retracted position with respect to distal end 18 of the tube structure 16 (FIG. 1) to an operative position extending directly from the distal end 18 and generally in the direction of axis A of the tube structure 16 (FIG. 2). A signal wire 24 is associated with each electrode 22 for obtaining signals from the electrodes as will be explained more fully below. The wires 24 extend within the tube structure 16 to the proximal end 20 thereof.

As shown in FIG. 1, when being inserted into the human organ 14, the electrodes 22 are in an insertion position. More particularly, the electrodes 22 are retracted, disposed near the distal end 18 of the tube structure 16. In the illustrated embodiment, the electrodes 22 are delivered into the lumen 28 of the stomach body 26 and/or antrum 30 in order to record myoelectrical activity from the stomach (or other hollow organ) 14 within the abdominal cavity.

Figure 3:
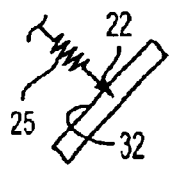
FIG. 3 is an enlarged view of an embodiment of an electrode of the invention.

The electrodes 22 are delivered on the tube structure 16 that is passed through the biopsy channel of a standard endoscope 12. In the illustrated embodiment. three electrodes 22 are provided. Each electrode 22 is preferably a recording electrode. Alternately, at least one electrode 22 can be a configured to delivery energy to the organ, for example, to electrically stimulate nerve muscle and other tissue of the stomach wall 32. Each electrode 22 is approximately 4 mm in length and 0.5 mm in diameter. The electrodes may be conventional and can be, for example, needle electrodes as disclosed in U.S. Pat. No. 6,006,755, the content of which is hereby incorporated into the present specification by reference. However, contractions can occur in the stomach or other hollow internal organ causing a "rolling" of the tissue of wall 32. Thus, as shown in FIG. 3, spring structure 25 is associated with each electrode 22 so that the electrodes can be resilient and flex with the rolling motion of the wall 32 during a contraction and maintain proper electrode contact. In the illustrated embodiment, the spring structure 25 is a coil structure. It can be appreciated, however, that the spring structure can be any structure that provides resilience to the electrode.

To move the electrodes between the retracted and extended positions, actuating structure 34, 36 is provided. In the embodiment, the actuating structure can be, for example, one or more wires 34 operatively associated with the electrodes 22 that are manually movable separately, or in unison at the proximal end of the tube structure 16. For example, FIG. 1 shows a single plunger 36 coupled to the wires 34. Movement of the plunger 36 extends and retracts the electrodes 22 in unison. Alternately, FIG. 2 shows a plunger 36' associated with each electrode 22 to move the electrodes 22 separately from each other so that the extent of the electrodes can be adjusted to engage a curved surface.

With reference to FIG. 2, when the tube structure 16 is placed in the desired position within the organ 14 via the endoscope, the electrodes 22 are extended via the actuating structure 34, 36 to impinge upon the mucosal lining or wall 32 or pierce the mucosa to a depth of preferably 2–4 mm. In the extended position, the electrodes are spaced apart between about 1–10 mm and are arranged substantially on a common curvilinear surface P. In this way gastric myoelectrical activity from the interstitial cells of Cajal and/or smooth muscle and/or enteric neurons are recorded from the three electrodes 22.

The output of each electrode 22 is a raw signal. In particular, the raw signal is a bioelectrical signal recorded from the lining 32 that reflects the myoelectrical activity of the stomach. The outputs of the electrodes 22 are sent to an amplifier 38 to amplify the raw analog signal. The amplified signal 40 is sent to a strip chart recorder 42 for a hard copy thereof. In addition, the amplified signal 40 is sent to an A/D converter 44 of a computer 46 for digitization of the analog signal for software analysis. In the Illustrated embodiment, the A/D converter 44 is a card of computer 46. It can be appreciated that the A/D converter 44 may be a device separate from the computer 46.

In addition, a ground is placed on the abdomen. Respiration rate from the patient is also detected via sensor 48 placed on the chest of the patient. An amplifier 50, preferably a conventional pressure transducer amplifier, is used to amplify an analog respiration signal from the respiration sensor 48. The amplified respiration signal 52 is sent to another channel of the strip chart recorder 42 to monitor artifact caused by respiration movements and/or body movements of the patient. The electrical recordings at each site within the organ 14 continue for at least 2 minutes but may continue as long as feasible. Data from the recorder 42 and computer 46 can be used by a physician to analyze the signals and perform clinically relevant analyses for interpretation to study myoelectric activity, as disclosed in U.S. Pat. No. 6,351,665, the contents of which is hereby incorporated into the present specification by reference.

When the initial electrical recording is completed in the organ 14, the electrodes 22 are retracted and the catheter structure 10 is moved to another site within the organ (e.g., stomach) 14. The electrodes 22 are again extended in the new area of the organ 14 in order to begin recording the next period.

With the catheter structure 10 of the invention:

1. The exact position or source of the gastric myoelectrical activity can be determined because the electrodes 22 are placed in the antrum or gastric body under direct vision via the endoscope 12;
2. The frequency and amplitude of the gastric myoelectrical activity are directly measured without interference from abdominal musculature, adipose tissue or skin;
3. The incidence of propagation and the propagation velocity of the gastric myoelectrical activity, in an ORAD or ABORAD direction, can be determined;
4. The electrical patterns in the fundus, body or antrum of the stomach in health can be MAPPED in order to determine normal electrical pathways; and
5. The electrical patterns in the fundus, body or antrum of the stomach in various diseases or disorders can be MAPPED and extent of damage to the gastric electrical network in these diseases and disorders can be determined.
6. Since the patient will be sedated and myoelectrical activity is monitored at the stomach lining, artifact caused by respiration will be less than that occurring in the EGG, but is still problematic. The artifact can be taken into account by using the respiration sensor 48.

The catheter structure 10 can be modified by changing the length thereof when designed for use in the following other organs:

1. Duodenum and jejunum
2. Bile duct
3. Rectum and sigmoid colon; terminal ileum, ascending and transverse colon;
4. Urinary bladder
5. Uterus and oviducts The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A catheter structure comprising:

an elongated tube structure having distal and proximal ends and an axis, electrodes associated with the tube structure and being constructed and arranged to be moved from a retracted position substantially within the tube structure to an extended position extended directly outwardly from the distal end of the tube structure and generally in the direction of the axis, the electrodes being constructed and arranged to obtain signals relating to myoelectrical activity of an intra-abdominal organ, and actuating structure operatively associated with the electrodes to move the electrodes between the extended and retracted positions, wherein a respiration sensor is provided in combination with the catheter structure to monitor respiration of a patient while the myoelectrical activity of the organ is being monitored.

2. The catheter structure of claim 1, wherein wires for obtaining signals from the electrodes extend within the tube structure to the proximal end thereof.

3. The catheter structure of claim 2, in combination with an amplifier, the wires being connected to the amplifier to amplify the signals from the electrodes.

4. The catheter structure of claim 3, in combination with a recorder and computer, wherein the amplified signals are sent to both the computer and the recorder for analysis of the myoelectrical activity.

5. The catheter structure of claim 4, wherein signals of the respiration sensor are sent to both the computer and the recorder to determine when artifact is present.

6. The catheter structure of claim 1, wherein the tube structure is constructed and arranged to pass through an endoscope.

7. The catheter structure of claim 1, wherein the actuating structure includes an actuating wire coupled to each electrode, the actuating wires being arranged to be moved so that the electrodes are moved between the retracted and extended positions in unison.

8. The catheter structure of claim 1, wherein the actuating structure is coupled to the electrodes and extends to the proximal end of the tube structure, the actuating structure being constructed and arranged to be manually moved to move the electrodes between the retracted and extended positions.

9. The catheter structure of claim 8, wherein the actuating structure is constructed and arranged to cause movement of the electrodes separately from each other.

10. The catheter structure of claim 1, wherein the electrodes are constructed and arranged to be disposed substantially on a common plane in the extended position.

11. The catheter structure of claim 1, further comprising spring structure associated with each electrode so as to provide resiliency to the electrodes and proper contact of the electrode in the event a contraction occurs in the organ.

12. A catheter structure comprising:

an elongated tube structure having distal and proximal ends and an axis, electrodes associated with the tube structure and being constructed and arranged to be moved from a retracted position substantially within the tube structure to an extended position extended directly outwardly from the distal end of the tube structure and generally in the direction of the axis, the electrodes being constructed and arranged to obtain signals relating to myoelectrical activity of an intra-abdominal organ, and actuating structure operatively associated with the electrodes to move the electrodes between the extended and retracted positions, wherein three electrodes are provided and adjacent electrodes are disposed between approximately 1–10 mm apart when in the extended position, and wherein a respiration sensor is provided in combination with the catheter structure to monitor respiration of a patient while the myoelectrical activity of the organ is being monitored.

13. A method of obtaining myoelectric activity from an intra-abdominal body organ having an internal cavity and a lining, the method including steps of:

providing catheter structure including an elongated tube structure having distal and proximal ends and an axis, electrodes associated with the tube structure and being constructed and arranged to be moved from a retracted position substantially within the tube structure to an extended position extended directly outwardly from the distal end of the tube structure and generally in the direction of the axis, the electrodes being constructed and arranged to obtain signals relating to myoelectrical activity of an intra-abdominal organ of a patient, and actuating structure operatively associated with the electrodes to move the electrodes between the extended and retracted positions, inserting the tube structure into the internal cavity of the organ, with the electrodes being in a retracted position with respect to a the distal end of the tube structure, moving the actuating structure to move the electrodes to the extended position to impinge on the lining of the organ, providing a respiration sensor to monitor respiration of the patient, recording signals from the electrodes indicative of myoelectrical activity of the organ, and recording signals from the respiration sensor while the signals from the electrodes are being recorded.

14. The method of claim 13, wherein the organ is the stomach and the step of extending the electrodes includes extending the electrodes to impinge on the mucosal lining of the stomach.

15. The method of claim 13, wherein the organ is the stomach and the step of extending the electrodes includes extending the electrodes to pierce the mucosal lining of the stomach to a depth of approximately 2–4 mm.

16. The method of claim 13, further including using an endoscope to place the catheter structure into the organ.

17. The method of claim 13, wherein at least one electrode is constructed and arranged to electrically stimulate tissue of the organ, the method electrically including stimulating tissue with the at least one electrode.

18. The method of claim 13, further comprising determining when artifact occurs based on the signals recorded from the respiration sensor.

19. The method of claim 13, further comprising interpreting a condition of the organ based on the recorded signals indicative of myoelectrical activity.

* * * * *